United States Patent [19]

Fujikawa et al.

[11] Patent Number: 5,101,829

[45] Date of Patent: Apr. 7, 1992

[54] SEMICONDUCTOR PRESSURE PULSE WAVE SENSOR

[75] Inventors: Kimio Fujikawa, Komaki; Chikao Harada, Nagoya, both of Japan

[73] Assignee: Colin Electronics Co., Ltd., Aichi, Japan

[21] Appl. No.: 630,076

[22] Filed: Dec. 19, 1990

[30] Foreign Application Priority Data

Jan. 9, 1990 [JP] Japan .................................. 2-2293

[51] Int. Cl.⁵ ............................................. A61B 5/02
[52] U.S. Cl. ................................ 128/672; 128/687; 128/690
[58] Field of Search ............... 128/680, 687, 688, 689, 128/690

[56] References Cited

U.S. PATENT DOCUMENTS

| | | | |
|---|---|---|---|
| 4,423,738 | 1/1984 | Newgard. | |
| 4,784,152 | 11/1988 | Shinoda | 128/690 |
| 4,802,488 | 2/1989 | Eckerle | 128/690 |
| 4,901,733 | 2/1990 | Kaida | 128/690 |
| 4,947,855 | 8/1990 | Yokoe et al. | 128/690 |
| 4,966,156 | 10/1990 | Perry | 128/687 |
| 4,987,900 | 1/1991 | Eckerle | 128/687 |

*Primary Examiner*—William E. Kamm
*Assistant Examiner*—Robert L. Nasser, Jr
*Attorney, Agent, or Firm*—Oliff & Berridge

[57] ABSTRACT

A semiconductor sensor for detecting a pressure pulse wave produced from an arterial vessel of a subject, including a semiconductor substrate including a thin portion obtained by locally forming a recess in one of opposite surfaces of the semiconductor substrate, at least one semiconductor pressure sensing element supported by the thin portion of the semiconductor substrate, for converting a pressure pulse wave transmitted from the arterial vessel to the thin portion, into an electric signal, and at least one semiconductor active element supported by the semiconductor substrate, for converting the electric signal into a different electric signal, the at least one active element including a portion of the semiconductor substrate.

22 Claims, 6 Drawing Sheets

SEMICONDUCTOR PRESSURE PULSE WAVE SENSOR

BACKGROUND OF THE INVENTION

1. Field of the Invention

The present invention generally relates to a pressure pulse wave sensor and particularly to the art of reducing the size of the pulse wave sensor.

2. Related Art Statement

Pressure pulse wave, namely, oscillatory pressure wave produced from an arterial vessel of a subject reflects not only blood pressure of the subject but also physiological or pathological condition of the circulatory organ of the same. Hence, it is desired to non-invasively detect pressure pulse wave produced from an arterial vessel of a subject, for measuring blood pressure of the subject or making a diagnosis on the circulatory organ of the same.

In the above background, a pressure pulse wave detecting apparatus has been proposed which is of the type adapted to non-invasively detect pressure pulse wave produced from an artery underlying the skin of a subject, by pressing the artery via the skin. Such an apparatus is disclosed by U.S. Pat. No. 4,423,738 issued to Newgard. The disclosed apparatus includes a pressure pulse wave sensor adapted to be set on the skin of a subject. The pulse wave sensor includes a semiconductor substrate, a plurality of pressure sensing elements supported by the semiconductor substrate, and a pressing means for pressing the semiconductor substrate against an arterial vessel of the subject via the skin of the same. The semiconductor substrate includes a plurality of thin portions each obtained by locally forming a recess in one of opposite surfaces of the substrate which one surface contacts the skin of the subject when the pulse wave sensor is set on the skin. Each thin portion supports a pressure sensing element, namely, Wheatstone bridge including, for example, four piezoresistors. Each bridge detects strain produced in the corresponding thin portion as a result of transmission thereto of the pressure pulse wave from the artery, and converts the strain into electric signal (hereinafter, referred to as the pulse wave signal). The pulse wave signals generated by those pressure sensing elements are converted or processed by active elements provided on a wiring substrate to which the semiconductor substrate is secured. Such active elements include a multiplexer which multiplexes the pulse wave signals into multiplexed signal, a preamplifier which amplifies the multiplexed signal, and an analog to digital (A/D) converter which converts the amplified multiplexed signal into digital signal, which in turn is analyzed by a computer of a main device of the pulse wave detecting apparatus.

As is apparent from the foregoing, in the above described conventional pulse wave detecting apparatus, at least some active elements such as a multiplexer and a preamplifier are supported by the wiring substrate to which the semiconductor substrate is secured, in order to reduce the number of cables or lead wires used to connect between the pulse wave sensor and the main device. Consequently, the overall size of the pulse wave sensor which is set on the skin of a subject cannot be reduced to a satisfactory level. This leads to large possibility that the pulse wave detection is adversely influenced by contact of the sensor with an external object, or physical motion of the subject together with the sensor.

SUMMARY OF THE INVENTION

It is therefore an object of the present invention to provide a pressure pulse wave sensor of a reduced size that is less often influenced by contacting an external thing, or being moved due to physical motion of a subject.

The above object has been achieved by the present invention, which provides a semiconductor sensor for detecting a pressure pulse wave produced from an arterial vessel of a subject, comprising (a) a semiconductor substrate including a thin portion obtained by locally forming a recess in one of opposite surfaces of the semiconductor substrate, (b) at least one semiconductor pressure sensing element supported by the thin portion of the semiconductor substrate, for converting a pressure pulse wave transmitted from the arterial vessel to the thin portion, into an electric signal, and (c) at least one semiconductor active element supported by the semiconductor substrate, for converting the electric signal into a different electric signal, the at least one active element including a portion of the semiconductor substrate.

In the semiconductor pressure pulse wave sensor constructed as described above, at least one active element which processes the electric signal produced from the at least one pressure sensing element, into a different electric signal, is supported by the semiconductor substrate such that the at least one active element is integral with the semiconductor substrate. Therefore, it is no longer required to support the at least one active element on a wiring substrate to which the semiconductor substrate is secured. Thus, the overall size of the semiconductor sensor is reduced. Accordingly, the semiconductor sensor is less often adversely influenced by contacting an external object, or being moved due to physical motion of a subject. Thus, the reliability of the pulse wave detection is improved.

According to an advantageous feature of the present invention, each of the at least one semiconductor pressure sensing element includes four resistors and four conductors which cooperate with each other to provide a Wheatstone bridge. In this case, each of the resistors and conductors may be provided by diffusion or injection of an impurity into the thin portion of the semiconductor substrate. Alternatively, the resistors and conductors may be such that each of the resistors is provided by diffusion or injection of an impurity into the thin portion of the semiconductor substrate, while each of the conductors is provided by vapor deposition of aluminum to the thin portion of the semiconductor substrate.

According to another feature of the present invention, at least one semiconductor pressure sensing element include a plurality of semiconductor pressure sensing elements which cooperate with each other to provide an array along a straight line, the at least one active element comprising a first and a second multiplexer each of which is connected to each of the pressure sensing elements and has a single output terminal. In this case, the semiconductor pressure sensing elements may consist of four pressure sensing elements, and each of the first and second multiplexers may include four analog switches which are connected to the corresponding pressure sensing elements, and four AND gates and two inverters which cooperate with each other to successively actuate the four analog switches so that a multiplexed signal is generated from the single output terminal of the each of the first and second multiplexers.

According to yet another feature of the present invention, the first and second multiplexers are provided by diffusion or injection of an impurity into a portion of the semiconductor substrate which portion is different from the thin portion.

According to a further feature of the present invention, the semiconductor sensor further comprises a power supply circuit and a preamplifier, the power supply circuit being connected to each of the pressure sensing elements to supply the each pressure sensing element with electricity, the multiplexed signal generated by each of the first and second multiplexers being amplified by the preamplifier. In this case, the semiconductor sensor may further comprise a wiring substrate which supports the power supply circuit and the preamplifier on one of opposite surfaces thereof, the semiconductor substrate being secured to the one surface of the wiring substrate.

In a preferred embodiment of the present invention, the power supply circuit and the preamplifier are supported by the semiconductor substrate, each of the power supply circuit and the preamplifier including a portion of the semiconductor substrate.

In another embodiment of the present invention, the semiconductor substrate is formed of single crystal silicon. The instant embodiment may further comprise a back-up plate formed of single crystal silicon, and the semiconductor substrate may be adhered to the the back-up plate with a silicone rubber adhesive. The embodiment may further comprise pressing means for pressing the semiconductor substrate against the arterial vessel via a body surface of the subject.

BRIEF DESCRIPTION OF THE DRAWINGS

The above and optional objects, features and advantages of the present invention will be better understood by reading the following detailed description of the presently preferred embodiments of the invention when considered in conjunction with the accompanying drawings, in which.

DETAILED DESCRIPTION OF THE PREFERRED EMBODIMENTS

There will be described in detail an embodiment of the present invention.

Figure 1:
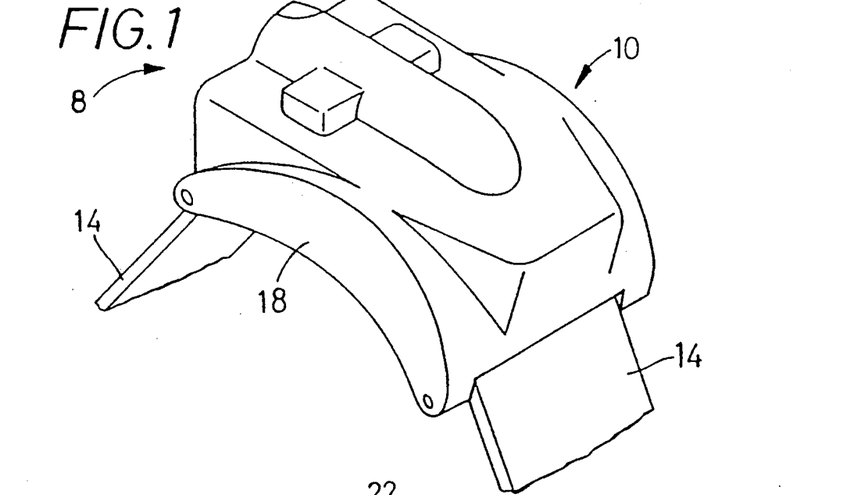
FIG. 1 is a view of a probe including a pressure pulse wave sensor embodying the present invention.

Referring first to FIG. 1, there is shown a probe 8 of a pulse wave detecting apparatus, including a pressure pulse wave sensor embodying the present invention. The probe 8 is worn on a wrist of a subject. The probe 8 includes a housing 10 formed of resin and having a configuration like a container. Longitudinal side walls 18, 20 (FIG. 3) of the housing 10 have a generally crescent shape, while a widthwise intermediate portion of a bottom wall of the housing 10 is outwardly protruded. The protruded portion extends parallel to the longitudinal side walls 18, 20. The probe 8 is detachably set on the wrist of the subject with the help of a pair of bands 14, 14 such that an open end of the housing 10 contacts a body surface 12 (FIG. 2) of the subject.

Figure 2:
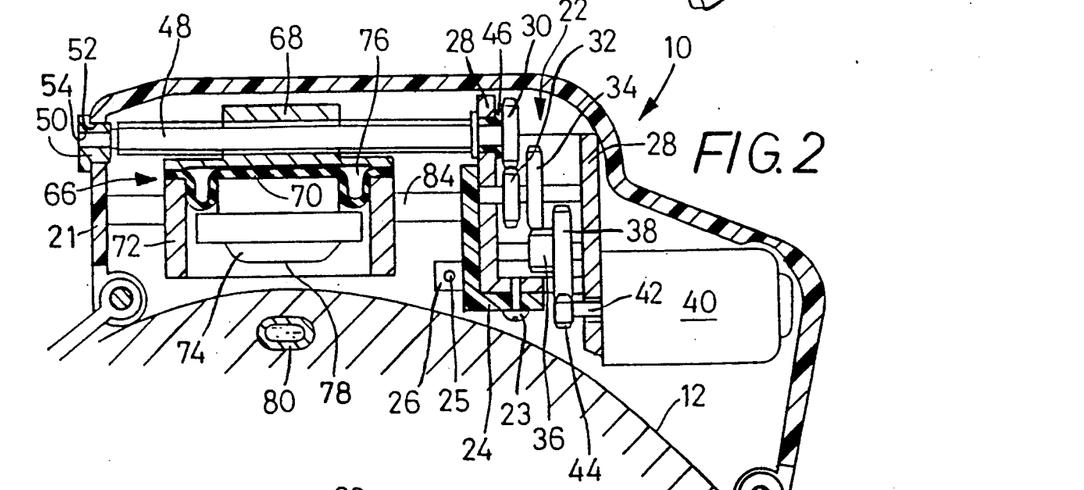
FIG. 2 is a longitudinal cross sectional view of the probe of FIG. 1.

Referring to FIG. 2, there is shown a reduction gear unit 22 secured with a screw 23 to a support plate 24. The support plate 24 is formed of a resin and has an L-shaped cross section. A pair of brackets 26 (only one of them is shown) extending from the support plate 24, are secured with screws 25 to the longitudinal side walls 18, 20 of the housing 10, respectively. Thus, the reduction gear unit 22 is fixed to the housing 10.

The reduction gear unit 22 includes six gear wheels 30, 32, 34, 36, 38, and 44. The first wheel 30 meshes with the second wheel 32, while the second wheel 32 is fixed to the third wheel 34 coaxially therewith. The third wheel 34 meshes with the fourth wheel 36, while the fourth wheel 36 is fixed to the fifth wheel 38 coaxially therewith. The fifth wheel 38 meshes with the sixth wheel 44, which is connected to an output shaft 42 of a drive motor 40. The second to fifth wheels 32, 34, 36, 38 are supported by a metal frame 28 such that each wheel is rotatable about an axis thereof.

The first wheel 30 is connected to one of opposite axial ends of a feed screw 48. The one axial end of the feed screw 48 is supported by the metal frame 28 via a bearing 46 formed of a resin. The bearing 46 is fitted in a hole formed through the frame 28. The feed screw 48 is rotatable with the first wheel 30. Thus, the feed screw 48 is operatively connected to the drive motor 40. That is, the feed screw 48 is driven or rotated by the drive motor 40. The drive motor 40 is secured to the metal frame 28.

A hole 52 is formed through a transverse side wall 21 of the housing 10. A cylindrical bearing 50 is fitted in the hole 52. The other axial end of the feed screw 48 opposite to the one axial end thereof fitted in the bearing 46, is rotatably supported by the side wall 21 via the cylindrical bearing 50. The feed screw 48 is disposed at a widthwise middle location in an inner space of the housing 10, so as to extend parallel to the longitudinal side walls 18, 20 of the housing 10.

The cylindrical bearing 50 has an eccentric hole 54 formed axially therethrough such that the hole 54 is eccentric with the axis of the bearing 50. By rotating the eccentric bearing 50 by an appropriate angle with an adjusting tool, the above indicated other axial end of the feed screw 48 fitted in the eccentric hole 54 of the bearing 50, is displaced upward, downward, leftward, or rightward along a predetermined circle to an appropriate position.

Figure 3:
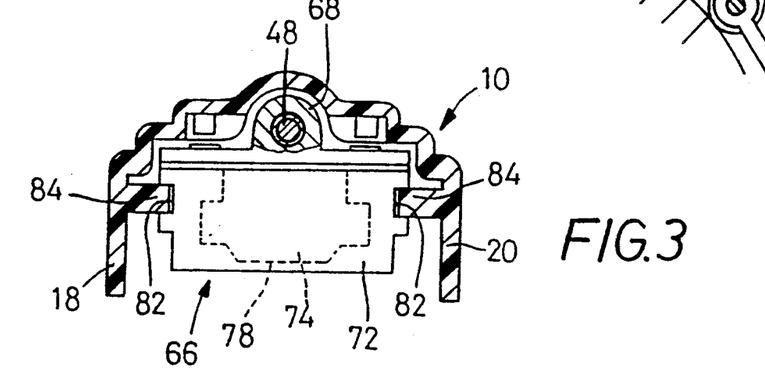
FIG. 3 is a transverse cross sectional view of the probe of FIG. 1.

As shown in FIGS. 2 and 3, the probe 8 includes a pressing device 66. The pressing device 66 includes an internally threaded, engage member 68, an elastic diaphragm 70 made of rubber, and a rectangular hollow member 72. The engage member 68 is engaged with the externally threaded feed screw 48. The hollow member 72 is secured to a lower face of the engage member 68 via the diaphragm 70. A pressure pulse wave sensor 74 is secured to a central portion of a lower surface of the diaphragm 70.

The engage member 68 and the diaphragm 70 cooperate with each other to define a pressure chamber 76, which communicates with a pressurized fluid supply device and a pressure regulate device (both not shown). When the pressure chamber 76 is supplied with a pressurized fluid from the supply device via the pressure regulate device, the pulse wave sensor 74 is pressed against the body surface 12 with a pressing force corresponding to a fluid pressure in the pressure chamber 76.

The pulse wave sensor 74 has a press surface 78 at which the sensor 74 is pressed against the body surface 12. The press surface 78 is defined by one of opposite surfaces of a semiconductor substrate 98 (FIG. 4) at which are provided a plurality of pressure sensing elements 100 (described later in detail) such as semiconductor resistors or pressure sensing diodes. The pulse wave sensor 74 is pressed against the body surface 12 to such an extent that an underlying arterial vessel (e.g., radial artery) 80 is partially flattened, that is, is so deformed as to have a flattened portion. In this situation, the pulse wave sensor 74 or each of the pressure sensing elements 100 detects a pressure pulse wave (hereinafter, referred to as the "pulse wave") which is produced from the arterial vessel 80 in synchronism with heartbeat of the subject and is transmitted to the press surface 78.

As clearly shown in FIG. 3, the rectangular hollow member 72 has a pair of straight guide grooves 82, 82 formed in outer surfaces of the side walls thereof opposed to the longitudinal side walls 18, 20 of the housing 10, while a pair of straight guide rails 84, 84 are provided on the inner surfaces of the longitudinal side walls 18, 20. The guide rails 84, 84 are engaged with the corresponding guide grooves 82, 82. When the feed screw 48 is rotated by the drive motor 40 with the probe 8 being set or the wrist 12 of the subject, the pressing device 66 is displaced without any disturbing rattles over a predetermined stroke or distance by being guided by the guide rails and grooves 84, 82 in a direction generally perpendicular to the arterial vessel 80.

As previously described, the feed screw 48 is connected at the one axial end thereof to the first wheel 30, and simultaneously is supported at the other axial end thereof by the eccentric bearing 50. Therefore, by changing the angular position of the "eccentric", cylindrical bearing 50 in the hole 52 of the side wall 21 or housing 10, the level at which the other axial end of the feed screw 48 is supported is changed along a predetermined circle. Consequently, the axis of the first wheel 30 fixed to the one axial end of the feed screw 48 is moved along a predetermined circle. When the probe 8 is fabricated, a distance between the axis of the first wheel 30 and the axis of the second wheel 32 can easily be adjusted to an appropriate value by rotating the eccentric bearing 50, whereby a suitable engagement between the first and second wheels 30, 32 is achieved.

Thus, the present probe 8 is free from a problem that the pulse wave sensor 74 is not smoothly moved because of a dimensional error on the distance between the axes of the first and second wheels 30, 32, and a problem that durability of the first and/or second wheel 30, 32 is lowered because of extraordinary wear thereof. In addition, since dimensional errors on the first and second wheels 30, 32 are easily eliminated by adjusting the eccentric bearing 50, the tolerances required for the parts associated with those members 30, 32 may not be so restrictive, whereby the cost of manufacture of the probe 8 is reduced.

Figure 4:
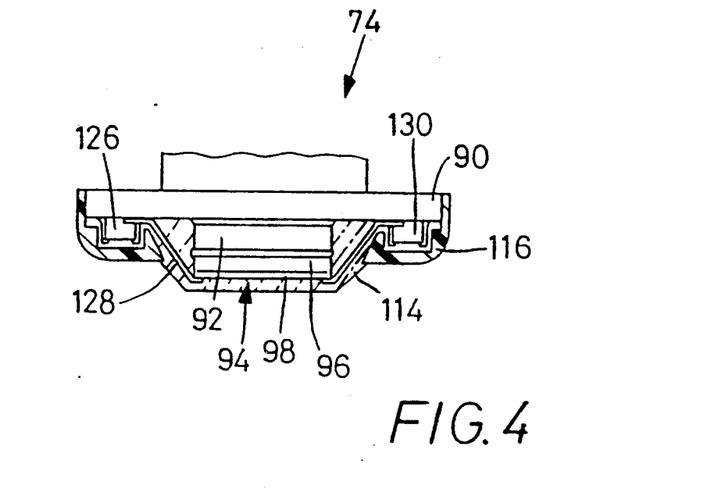
FIG. 4 is a cross sectional view of an essential part of the pulse wave sensor of the probe of FIG. 1, illustrating the details of the pulse wave sensor.

As shown in FIG. 4, the pulse wave sensor 74 includes a wiring substrate 90 formed of a ceramic, a spacer member 92, and a presser plate 94. The ceramic substrate 90 supports conductor patterns superposed one on another. The spacer member 92 is formed of an electrically insulating material such as ceramic or resin, and is adhered to the ceramic substrate 90. The presser plate 94 is supported by the insulator spacer 92. The pulse wave sensor 74 is pressed at the presser plate 94 (or press surface 78 thereof) against the body surface 12 of the subject.

Figure 5:
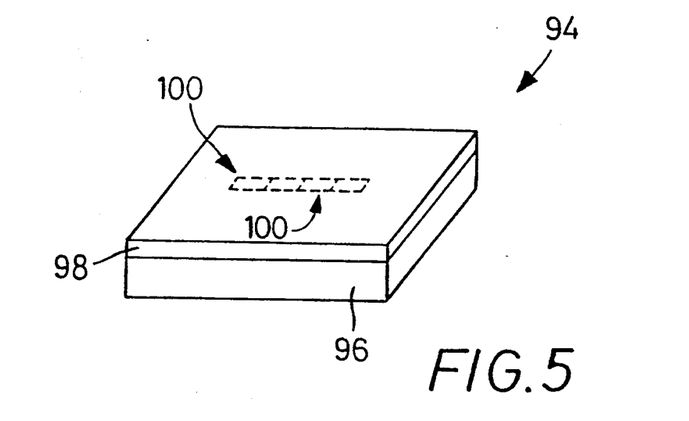
FIG. 5 is a perspective view of a presser plate of the pulse wave sensor of FIG. 4.

As shown in FIG. 5, the presser plate 94 includes a back-up plate 96 formed of a rigid material, and a semiconductor substrate 98 which is adhered to one of opposite surfaces of the back-up plate 96. The adhesion of the semiconductor substrate 98 to the back-up plate 96 is carried out by using an epoxy resin or a silicone rubber. The back-up plate 96 is formed by using a glass, or a plate formed of the same material as that of the semiconductor substrate 98 and having a greater thickness than that of the substrate 98. For minimizing the adverse influence due to difference in thermal expansion between the materials of back-up plate and semiconductor substrate 96, 98, it is preferred to use a silicone rubber adhesive to an epoxy resin adhesive. To the same end, it is preferred to use for the back-up member 96 a semiconductor thick plate to a glass plate. It is therefore the most recommendable that the semiconductor substrate 98 be adhered to the semiconductor back-up plate 96 by using the silicone rubber adhesive.

The back-up plate 96 has a high rigidity because of having a great thickness of 500 to 1500 $\mu$m (microns). Two holes (not shown) are formed through the back-up plate 96, for communicating the other or rear surface of the semiconductor substrate 98 opposite to the press surface 78, with ambient air under atmospheric pressure via central holes (not shown) formed through the insulator spacer 92 and ceramic substrate 90. The semiconductor substrate 90 has a thickness of about 300 $\mu$m. An elongate thin portion or diaphragm portion 106 (FIG. 6) is provided in the rear surface thereof communicating with the ambient air, by locally forming an elongate recess in the rear surface. The diaphragm portion 106 has a thickness of from several microns to ten and from several microns. The semiconductor substrate 98 is constituted by a single crystal silicon, for example.

As shown in FIG. 5, an array of pressure sensing elements 100 each for detecting a pressure applied thereto, are provided along a straight line in a central portion of the semiconductor substrate 98. In the present embodiment, four pressure sensing elements 100 are used. The pulse wave sensor 74 is pressed on the body surface 12 such that the array of pressure sensing elements 100 cross over the underlying arterial vessel 80, in a direction generally perpendicular thereto.

Figure 6:
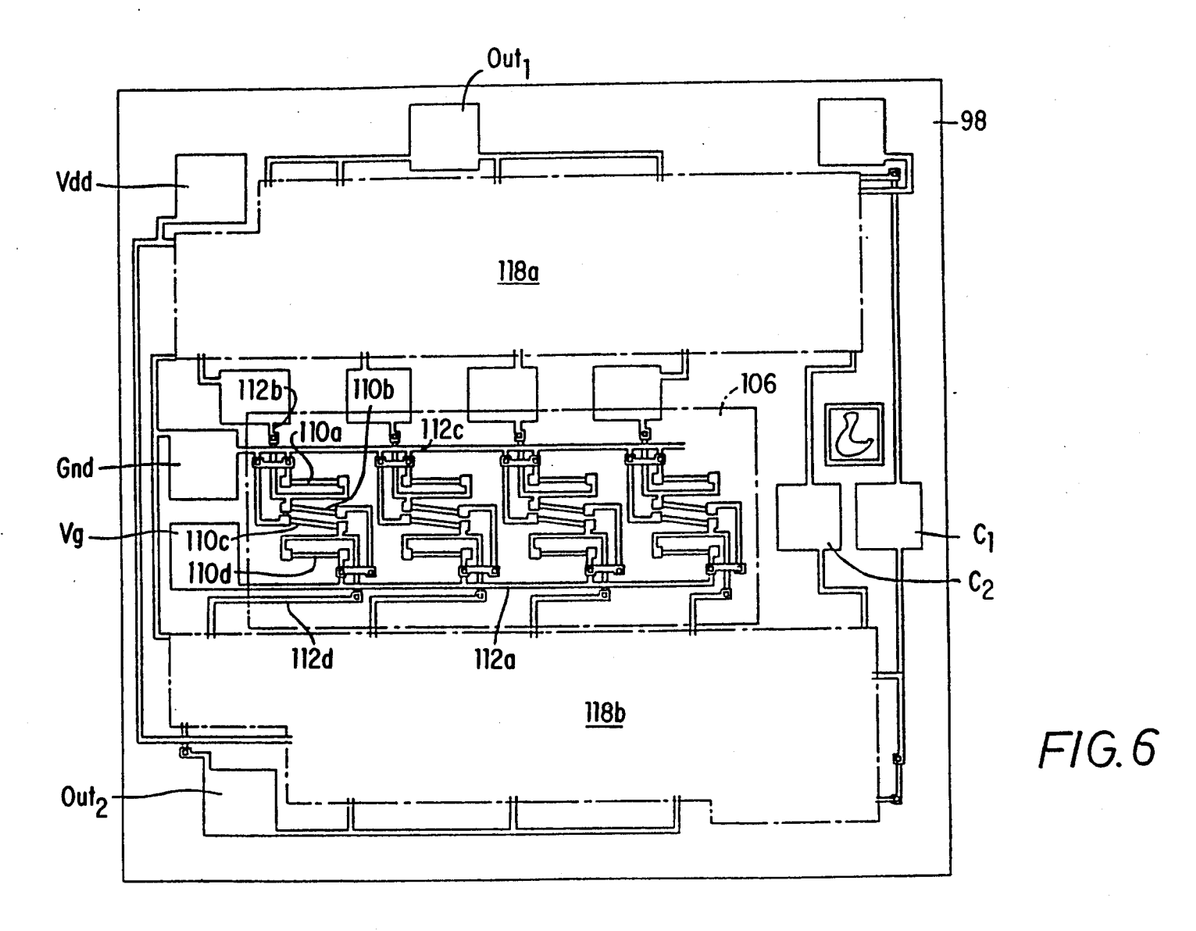
FIG. 6 is a view of a wiring pattern supported by a semiconductor plate of the pulse wave sensor of FIG. 4.
Figure 7:
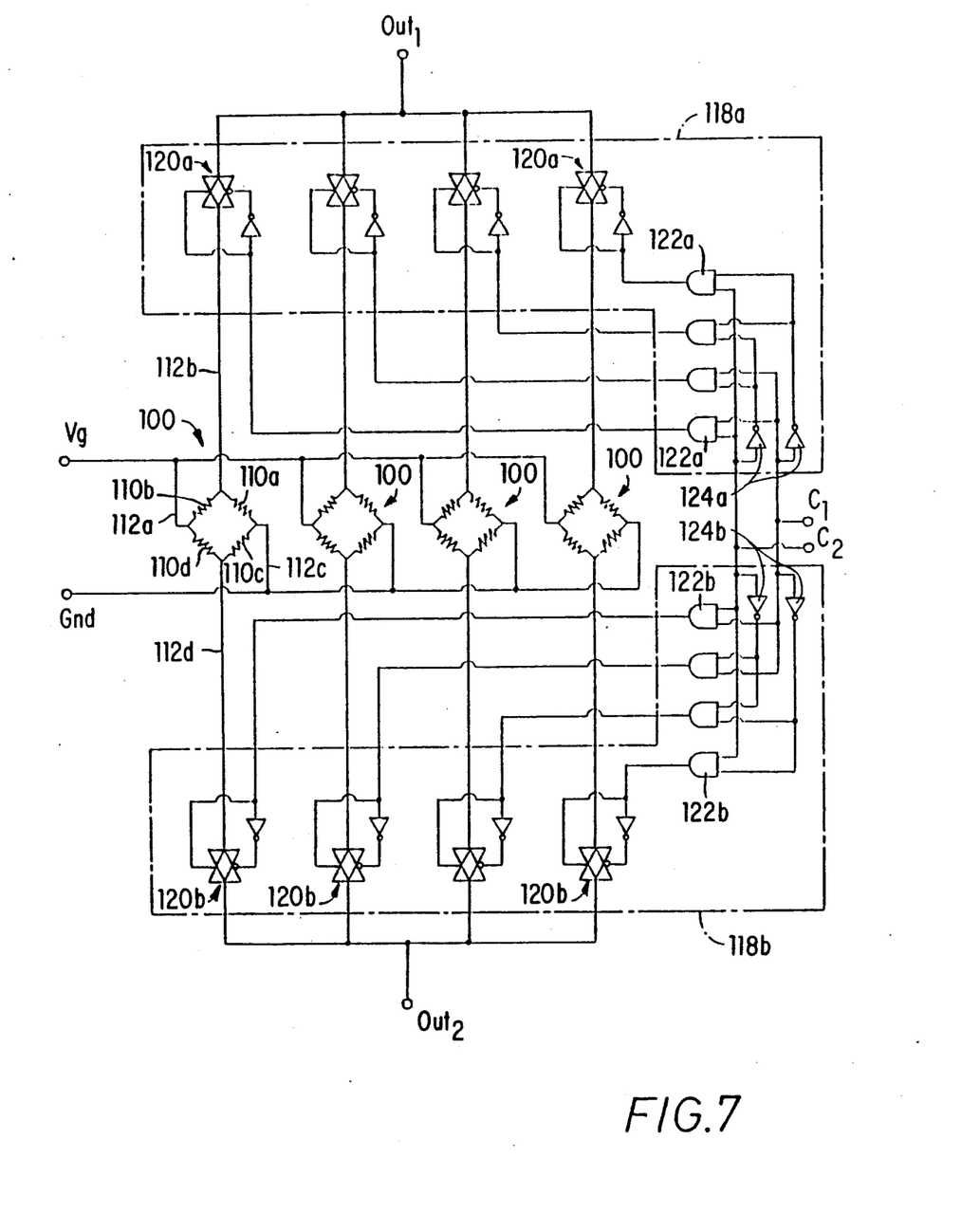
FIG. 7 is a view of a circuit diagram of the wiring pattern of FIG. 6.

Referring next to FIG. 6, there is shown a wiring pattern provided integrally with the semiconductor substrate 98, as viewed from the press surface 78 thereof. FIG. 7 is a circuit diagram of the wiring pattern. At the diaphragm portion 106, the four pressure sensing elements 100 are provided at regular intervals of 200 to 250 μm which intervals are sufficient to protect each element 100 against cross talk, namely, interference due to the strain produced in its adjacent element or elements 100 as a result of transmission thereto of pulse wave from the arterial vessel 80.

Each of the four pressure sensing elements 100 includes four semiconductor resistors 110a, 110b, 110c, 110d, and four semiconductor conductors 112a, 112b, 112c, 112d which cooperate with the four resistors 110 to constitute a Wheatstone bridge. The resistors 110 are formed by a known semiconductor manufacturing process, for example, diffusion or injection of a suitable impurity into the substrate 98. The conductors 112 are also formed by a known semiconductor manufacturing process such as diffusion or injection of a suitable impurity into the substrate 98, or vapor deposition of aluminum onto the substrate 98. A concentration of the impurity contained in the resistors 110 is different from that of the impurity contained in the conductors 112. The Wheatstone bridge constituted by the resistors and conductors 110, 112 generates an electric signal representing the strain produced at a corresponding region of the diaphragm portion 106 of the semiconductor substrate 98 at which region the bridge is provided. The strain is caused by a pressure pulse wave transmitted from the arterial vessel 80 to the bridge. Thus, each of the four bridges serves as a pressure sensing element 100. Since the resistors 110 and/or conductors 112 are formed by locally adding an impurity to, or increasing the concentration of an impurity in, the diaphragm portion 106 of the semiconductor substrate 98, the bridge includes invisible portions.

As shown in FIG. 6, on both sides of the array of the four pressure sensing elements 100, are provided a first and a second multiplexer 118a, 118b, respectively. The first and second multiplexers 118a, 118b cooperate with each other to multiplex by time sharing the output signals from the four bridges 100 into two multiplexed signals and generate the two signals via a pair of terminals OUT$_1$ and OUT$_2$, respectively. The two multiplexers 118a, 118b are provided in a portion of the semiconductor substrate 98 which portion is free from the diaphragm portion 106, by a known semiconductor manufacturing technique as described above.

As shown in FIG. 7, the first multiplexer 118a includes four analog switches 120a, and in addition, four AND gates 122a and two inverters 124a for successively and periodically actuating the four analog switches 120a according to four different combinations obtained by supplying each of two control terminals C$_1$ and C$_2$ with two different control signals. Meanwhile, the second multiplexer 118b includes four analog switches 120b, and in addition, four AND gates 122b and two inverters 124b for successively and periodically actuating the four analog switches 120b according to the four combinations obtained by supplying each of the two control terminals C$_1$ and C$_2$ with the two control signals.

As shown in FIG. 4, in the present pressure pulse wave sensor 74, a bridge power supply circuit 126 supplying the bridges 100 with an electric power V$_g$ (FIGS. 6 and 7), and in addition, a preamplifier 130 are provided or packaged together with superposed conductor patterns by soldering or wire bonding on the one surface of the ceramic substrate 90 to which one surface the semiconductor substrate 98 is secured. The various terminals or pads on the semiconductor substrate 98 are connected to corresponding terminals or pads provided on the ceramic substrate 90 via a flexible flat cable 128. The flat cable 128 includes a pattern of conductor wires arranged at regular intervals. The flat cable 128 is fabricated by, for example, etching a copper foil adhered to one surface of a polyimide-resin film and plating, with gold or its alloy, ends of the thus obtained conductor wires so as to provide terminals. In FIG. 6, a power supply for the multiplexers 118a, 118b is indicated at V$_{dd}$, and the earth for the bridges 100 is indicated at G$_{nd}$, respectively.

One end of the flat cable 128 is connected by thermal compression bonding or supersonic compression bonding to the terminals or pads arranged on the press surface 78 of the semiconductor substrate 98. After the semiconductor substrate 98 is connected to the ceramic substrate 90 as described above, the press surface 78 of the substrate 98 is coated with a resin 114 of low rigidity. Meanwhile, the bridge power supply circuit 126 and preamplifier 130 are covered and protected by a resin 116 of high rigidity.

Figure 8:
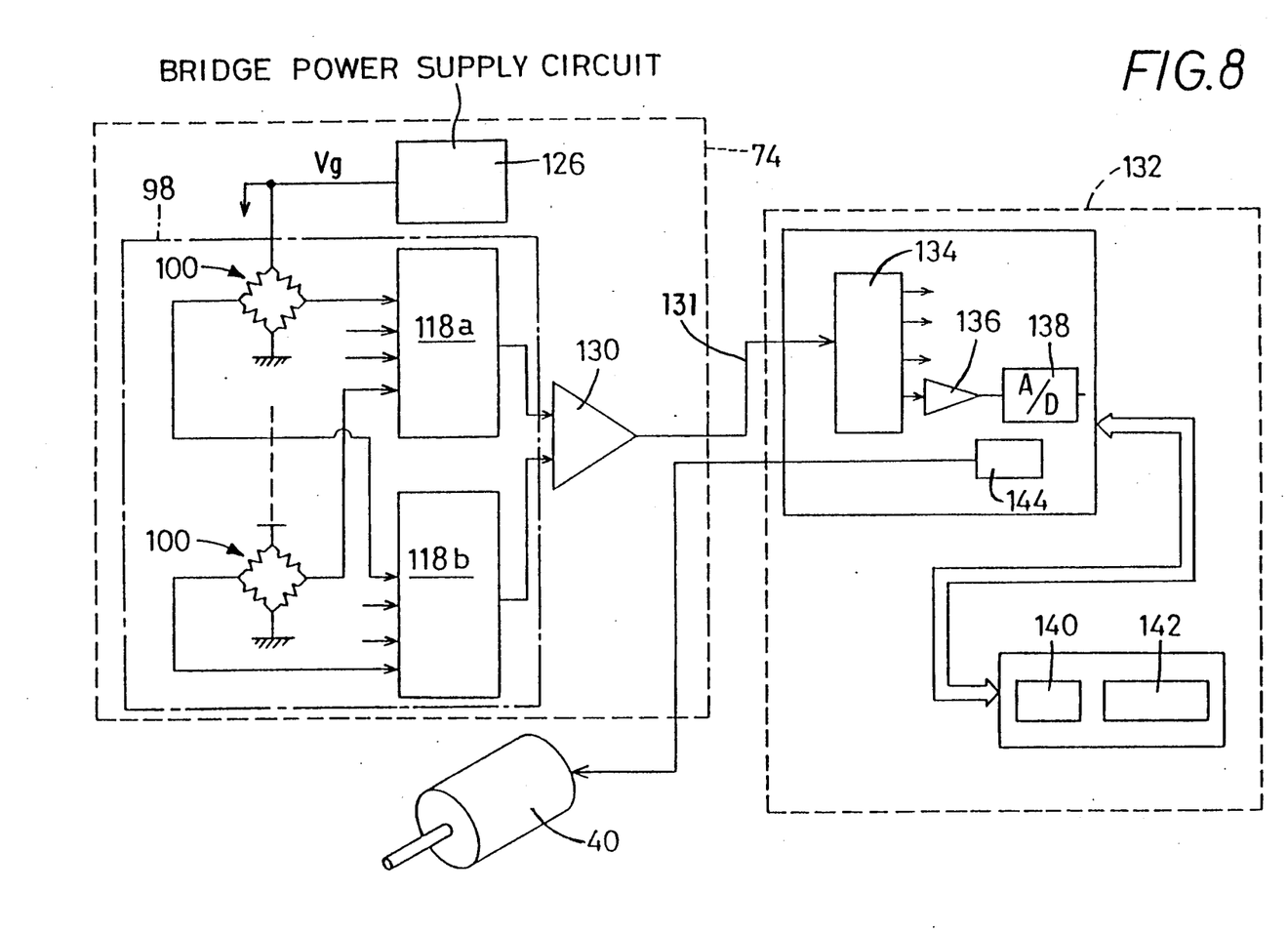
FIG. 8 is a diagrammatic view of an electric arrangement of a pulse wave detecting apparatus which includes the probe of FIG. 1.

Referring next to FIG. 8, there is shown an electric arrangement of the present pulse wave detecting apparatus, including the pulse wave sensor 74. In the figure, the output signals, namely, pulse wave signals generated from the four pressure sensing elements or bridges 100 provided integrally with the semiconductor substrate 98, are multiplexed by time-sharing by the first and second multiplexers 118a, 118b, and the multiplexed signals are amplified by the preamplifier 130. Then, the signals are demultiplexed into four analog signals or channels corresponding to the four pressure sensing elements 100, by a demultiplexer 134 of a main device 132 of the pulse wave detecting apparatus. A cable 131 connects between the probe 8 or pulse wave sensor 74, and the main device 132.

Each of the four analog signals is amplified by an amplifier 136, and then is converted into digital signal by an analog to digital (A/D) converter 138. The digital signal is supplied to a control unit 140. The control unit 140 is constituted by a microcomputer including a central processing unit (CPU), a read only memory (ROM), a random access memory (RAM), and an input-/output interface. The CPU processes input signals supplied thereto according to programs stored in the ROM by utilizing temporary storage function of the RAM. The CPU controls the operation of the drive motor 40 via a motor drive circuit 144 so that the pulse wave sensor 74 is moved to a position directly above the arterial vessel 80, and controls the operation of the pressing device 66 via a pressure regulate circuit (not shown) so that a portion of the wall of the arterial vessel 80 is flattened. In addition, the CPU selects, as an optimum pulse wave signal, one of the four channels which channel is coupled to a pressure sensing element 100 directly above the arterial vessel 80. The CPU commands a display 142 to indicate a waveform corresponding to the optimum pulse wave signal on a cathode ray tube (CRT) of the display 142. Furthermore, the CPU determines a systolic and a diastolic blood pressure of the subject based on an upper peak magnitude and a lower peak magnitude of the waveform, and commands the display 142 to indicate the determined blood pressure values.

As is apparent from the foregoing description, in the pulse wave sensor 74 of the present apparatus, the semiconductor substrate 98 supports not only the pressure sensing elements 100 but also the multiplexers 118a, 118b. The multiplexers 118a, 118b are formed integrally with the semiconductor substrate 98. The multiplexers 118a, 118b are an active element for processing an electric signal to a different electric signal. Since the semiconductor substrate 98 supports the multiplexers 118a, 118b, the ceramic substrate 90 no longer is required to support those active elements.

Figure 10:
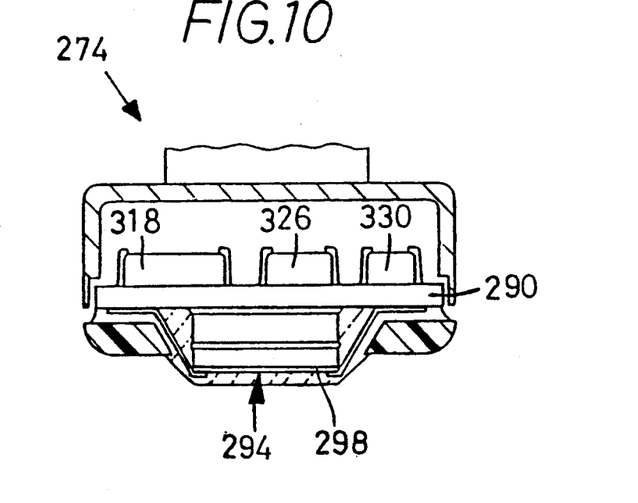
FIG. 10 is a view of a conventional pulse wave sensor, corresponding to FIG. 4.

In contrast thereto, in a conventional pressure pulse wave sensor 274 shown in FIG. 10, a semiconductor substrate 298 supports pressure sensing elements (not shown), but does not support any active element. The active elements such as multiplexers 318 are supported by a ceramic substrate 290. A bridge power supply circuit 326 and a preamplifier 330 are also supported by the ceramic substrate 290.

The overall size, and in particular thickness, of the pulse wave sensor 74 of the present detecting apparatus is reduced since the multiplexers 118a, 118b are supported by the semiconductor substrate 98, as compared with those of the above indicated conventional pulse wave sensor 274 in which the multiplexers 318 are supported by the ceramic substrate 290. Therefore, the pulse wave sensor 74 is less often adversely influenced by contacting an external object, or being moved due to physical motion of the subject. Thus, the reliability of the pulse wave detection is improved.

Figure 9:
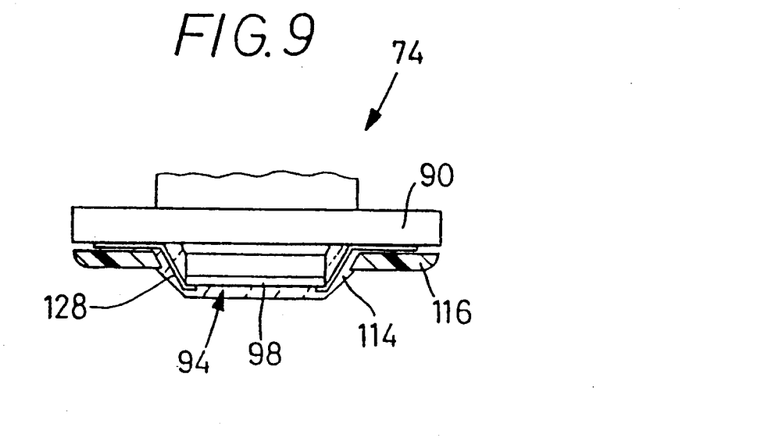
FIG. 9 is a view of another embodiment of the present invention, corresponding to FIG. 4.

Referring next to FIG. 9, there is shown a modified form of the pulse wave sensor 74. In this pulse wave sensor 74, a semiconductor substrate 98 supports a preamplifier and a bridge power supply circuit, in addition to pressure sensing elements and multiplexers (all not shown). Namely, those active elements are formed integrally with the semiconductor substrate 98. In this case, the overall size of the pulse wave sensor 74 is still reduced since a ceramic substrate 90 is not required to support those active elements.

While the present invention has been described in its preferred embodiments, the present invention may be embodied with various changes.

While, in the illustrated embodiments, the pressure sensing elements 100 are provided at regular intervals at the single, elongate thin or diaphragm portion 106, it is possible to provide pressure sensing elements at respective separate thin portions obtained by forming a plurality of recesses. In addition, it is possible to obtain a thin or diaphragm portion by forming a recess in the press surface 78. In this case, the recess may be filled by a filler formed of, for example, silicone rubber.

Although in the illustrated embodiments a single crystal silicon plate is used for the semiconductor substrate 98, it is possible to use for the semiconductor substrate 98 a single crystal plate of a compound semiconductor such as gallium arsenide.

It is to be understood that the present invention may be embodied with other changes, modifications and improvements that may occur to those skilled in the art without departing from the spirit and scope of the present invention as defined in the appended claims.

What is claimed is:

1. A semiconductor sensor for detecting a pressure pulse wave produced from an arterial vessel of a subject, comprising:

a semiconductor substrate including a thin portion obtained by locally forming a recess in one of opposite surfaces of the semiconductor substrate;

at least one semiconductor pressure sensing element supported by said thin portion of said semiconductor substrate, for converting a pressure pulse wave transmitted from said arterial vessel to said thin portion, into an electric signal; and at least one semiconductor active element supported by said semiconductor substrate, for converting said electric signal into a different electric signal, said at least one active element including a portion of said semiconductor substrate.

2. The sensor as set forth in claim 1, wherein each of said at least one semiconductor pressure sensing element includes four resistors and four conductors which cooperate with each other to provide a Wheatstone bridge.

3. The sensor as set forth in claim 2, wherein each of said resistors and conductors is provided by diffusion of an impurity into said thin portion of said semiconductor substrate.

4. The sensor as set forth in claim 2, wherein each of said resistors is provided by diffusion of an impurity into said thin portion of said semiconductor substrate, while each of said conductors is provided by vapor deposition of aluminum to said thin portion of said semiconductor substrate.

5. The sensor as set forth in claim 2, wherein each of said resistors and conductors is provided by injection of an impurity into said thin portion of said semiconductor substrate.

6. The sensor as set forth in claim 2, wherein each of said resistors is provided by injection of an impurity into said thin portion of said semiconductor substrate, while each of said conductors is provided by vapor deposition of aluminum to said thin portion of said semiconductor substrate.

7. The sensor as set forth in claim 1, wherein said at least one semiconductor pressure sensing element include a plurality of semiconductor pressure sensing elements which cooperate with each other to provide an array along a straight line, said at least one active element comprising a first and a second multiplexer each of which is connected to each of said pressure sensing elements and has a single output terminal.

8. The sensor as set forth in claim 7, wherein said semiconductor pressure sensing elements consist of four pressure sensing elements, each of said first and second multiplexers including four analog switches which are connected between corresponding pressure sensing elements, respectively, and the corresponding single output terminal, said each of said first and second multiplexers further including four AND grates connected to an input of the corresponding analog switches, respectively, and two inverters each of which is connected to an input of each of two of said four AND gates, said four AND gates and said two inverters cooperating with each other to successively actuate said four analog switches so that a multiplexed signal is generated from the single output terminal of said each of said first and second multiplexers.

9. The sensor as set forth in claim 7, wherein said first and second multiplexers are provided by injection of an impurity into a portion of said semiconductor substrate which portion is different from said thin portion.

10. The sensor as set forth in claim 7, wherein said first and second multiplexers are provided by diffusion of an impurity into a portion of said semiconductor substrate which portion is different from said thin portion.

11. The sensor as set forth in claim 7, further comprising a power supply circuit and a preamplifier, each of said pressure sensing elements including four resistors and four conductors which cooperate with each other to provide a Wheatstone bridge, said power supply circuit being connected to each Wheatstone bridge of each of said pressure sensing elements to supply said each Wheatstone bridge with electricity, said preamplifier being connected to the single output terminal of said each of said firth and second multiplexers to amplify the multiplexed signal generated by said each of said first and second multiplexers.

12. The sensor as set forth in claim 11, further comprising a wiring substrate which supports said power supply circuit and said preamplifier on a first surface thereof, said semiconductor substrate being secured to said first surface of said wiring substrate.

13. The sensor as set forth in claim 12, wherein said wiring substrate is formed of a ceramic.

14. The sensor as set forth in claim 12, further comprising a spacer member formed of an electrically insulating material, said spacer member being inserted between said semiconductor substrate and said wiring substrate.

15. The sensor as set forth in claim 11, wherein said power supply circuit and said preamplifier are supported by said semiconductor substrate, each of said power supply circuit and said preamplifier including a portion of said semiconductor substrate.

16. The sensor as set forth in claim 1, wherein said semiconductor substrate is formed of single crystal silicon.

17. The sensor as set forth in claim 16, further comprising a back-up plate formed of single crystal silicon, said semiconductor substrate being adhered to said back-up plate with a silicone rubber adhesive.

18. The sensor as set forth in claim 1, further comprising pressing means for pressing said semiconductor substrate against said arterial vessel via a body surface of said subject.

19. A semiconductor sensor for detecting a pressure pulse wave produced from an arterial vessel of a subject, comprising:
a semiconductor substrate including at lest one thin portion obtained by locally forming at least one recess in one of opposite surfaces of the semiconductor substrate;
a plurality of semiconductor pressure sensing elements supported by said at least one thin portion of said semiconductor substrate, each of said pressure sensing elements converting said pressure pulse wave transmitted from said arterial vessel to said at least one thin portion, into an electric signal; and
at least one semiconductor active element supported by said semiconductor substrate, for converting said electric signal into a different signal, said at least one active element including a portion of said semiconductor substrate which portion is different from said at least one thin portion, said at least one active element comprising a first and a second multiplexer each of which is connected to each of said pressure sensing elements and has a single output terminal.

20. The sensor as set forth in claim 19, wherein said at least one recess formed in said one surface of said semiconductor substrate consists of a single recess, and said at least one thin portion of said semiconductor substrate consists of a single thin portion.

21. A semiconductor sensor for detecting a pressure pulse wave produced from an arterial vessel of a subject, comprising:
a semiconductor substrate including a thin portion obtained by locally forming a recess in one of opposite surfaces of the semiconductor substrate;
four semiconductor pressure sensing elements supported by said thin portion of said semiconductor substrate, for converting said pressure pulse wave transmitted from said arterial vessel to said thin portion, into an electric signal; and
at least one semiconductor active element supported by said semiconductor substrate, for converting said electric signal into a different signal, said at least one active element including a portion of said semiconductor substrate, said at least one active element comprising a first and a second multiplexer each of which is connected to each of said four pressure sensing elements and has a single output terminal, said each of said first and second multiplexers including four analog switches which are connected between a corresponding pressure sensing element, respectively, and the corresponding single output terminal, said each multiplexer further including four AND gates connected to an input of the corresponding analog switches, respectively, and two inverters each of which is connected to an input of each of two of said four AND gates, said four AND gates and said two inverters cooperating with each other to successively actuate said four analog switches so that a multiplexed signal is generated from the single output terminal of said each multiplexer.

22. A semiconductor sensor for detecting a pressure pulse wave produced from an arterial vessel of a subject, comprising:
a semiconductor substrate including a thin portion obtained by locally forming a recess in one of opposite surfaces of the semiconductor substrate, wherein said semiconductor substrate is formed of single crystal silicon;
a back-up plate formed of single crystal silicon, said semiconductor substrate being attached to said back-up plate with a silicone rubber adhesive;
at least one semiconductor pressure sensing element supported by said thin portion of said semiconductor substrate, for converting said pressure pulse wave transmitted from said arterial vessel to said thin portion, into an electric signal; and
at least one semiconductor active element supported by said semiconductor substrate, for converting said electric signal into a different signal, said at least one active element including a portion of said semiconductor substrate.

* * * * *